(12) United States Patent
Ou et al.

(10) Patent No.: US 10,415,976 B2
(45) Date of Patent: Sep. 17, 2019

(54) METHOD AND APPARATUS FOR PROCESSING WEARING STATE OF WEARABLE DEVICE

(71) Applicant: BEIJING GALAXY RAINTAI TECHNOLOGY CO., LTD., Beijing (CN)

(72) Inventors: Lingxiao Ou, Beijing (CN); Wenwen Yan, Beijing (CN)

(73) Assignee: BEIJING GALAXY RAINTAI TECHNOLOGY CO., LTD., Beijing (CN)

( * ) Notice: Subject to any disclaimer, the term of this patent is extended or adjusted under 35 U.S.C. 154(b) by 293 days.

(21) Appl. No.: 15/314,062

(22) PCT Filed: Dec. 7, 2015

(86) PCT No.: PCT/CN2015/096536
§ 371 (c)(1),
(2) Date: Nov. 25, 2016

(87) PCT Pub. No.: WO2016/091131
PCT Pub. Date: Jun. 16, 2016

(65) Prior Publication Data
US 2017/0191835 A1 Jul. 6, 2017

(30) Foreign Application Priority Data
Dec. 9, 2014 (CN) .......................... 2014 1 0750858

(51) Int. Cl.
*G01C 21/16* (2006.01)
*G01C 19/5776* (2012.01)
(Continued)

(52) U.S. Cl.
CPC ............ *G01C 21/16* (2013.01); *A61B 5/1071* (2013.01); *A61B 5/1116* (2013.01); *A61B 5/681* (2013.01);
(Continued)

(58) Field of Classification Search
USPC ........................................................ 702/151
See application file for complete search history.

(56) References Cited

U.S. PATENT DOCUMENTS

| 2012/0188158 A1 | 7/2012 | Tan et al. |
| 2014/0278208 A1* | 9/2014 | Donaldson ........... A61B 5/7264 702/141 |

(Continued)

FOREIGN PATENT DOCUMENTS

| CN | 103105945 | 5/2013 |
| CN | 103267524 | 8/2013 |

(Continued)

OTHER PUBLICATIONS

From Chinese Application No. 201410750858.X, Office Action dated Jun. 3, 2015 and its English translation provided by Espacenet.

(Continued)

*Primary Examiner* — Paul D Lee
(74) *Attorney, Agent, or Firm* — Ladas & Parry, LLP (57) ABSTRACT

The present invention relates to a method and apparatus for processing a wearing state of a wearable device. Embodiments of the present invention achieve the purpose of obtaining an actual wearing state of the wearable device by obtaining a space quaternion parameter of the wearable device worn by the user, then obtaining a posture angle of the wearable device according to the space quaternion parameter, and then obtaining a measurement wearing state of the wearable device according to the posture angle of the wearable device.

7 Claims, 2 Drawing Sheets

(51) Int. Cl.
G06F 1/16 (2006.01)
A61B 5/00 (2006.01)
A61B 5/107 (2006.01)
A61B 5/11 (2006.01)
G04C 3/00 (2006.01)
G06F 3/01 (2006.01)
G16H 40/63 (2018.01)
G02B 27/01 (2006.01)

(52) U.S. Cl.
CPC ............ *A61B 5/70* (2013.01); *G01C 19/5776* (2013.01); *G04C 3/002* (2013.01); *G06F 1/163* (2013.01); *G06F 3/011* (2013.01); *G16H 40/63* (2018.01); *A61B 2562/0219* (2013.01); *G02B 27/017* (2013.01)

(56) References Cited

U.S. PATENT DOCUMENTS

| | | | | |
|---|---|---|---|---|
| 2015/0164430 | A1* | 6/2015 | Hu | A61B 5/7264 600/595 |
| 2016/0034817 | A1* | 2/2016 | Ali | H04M 1/72569 706/46 |
| 2017/0278262 | A1* | 9/2017 | Kawamoto | B64C 39/02 |

FOREIGN PATENT DOCUMENTS

| | | |
|---|---|---|
| CN | 103267524 A | 8/2013 |
| CN | 103976854 | 8/2014 |
| CN | 103976864 | 8/2014 |
| CN | 104127187 A | 11/2014 |
| CN | 104133550 A | 11/2014 |
| CN | 104407709 A | 3/2015 |
| EP | 2141632 | 1/2010 |

OTHER PUBLICATIONS

From PCT/CN2015/096536, Written Opinion dated Jun. 1, 2016 and its English translation provided by WIPO.
From PCT/CN2015/096536, CH. 1 International Preliminary Report on Patentability (IPRP) dated Jun. 22, 2017 and its English translation provided by WIPO.
First Search of the State Intellectual Property Office of the P.R.C. for application No. 201410750858.X, dated May 21, 2015.
Office Action of the State Intellectual Property Office of the P.R.C. for application No. 201410750858.X, dated Mar. 6, 2015, and its English translation provided by Espacenet.
International Search Report for PCT/CN2015/096536 dated Jan. 21, 2016 and its English machine translation provided by WIPO.
Written Opinion for PCT/CN2015/096536 dated Jan. 21, 2016 and its English machine translation provided by Google Translate.
First Search of the State Intellectual Property Office of the P.R.C. for application No. 201410750858X.
Office Action of the State Intellectual Property Office of the P.R.C. for application No. 201410750858X and its English machine translation provided by Google Translate.

* cited by examiner

METHOD AND APPARATUS FOR PROCESSING WEARING STATE OF WEARABLE DEVICE

CROSS-REFERENCE TO RELATED APPLICATIONS

The present application is the U.S. national phase of PCT Application PCT/CN2015/096536 filed on Dec. 7, 2015, which claims priority to the Chinese patent application No. 201410750858.X entitled "Method and Apparatus for Processing Wearing State of Wearable Device" filed on Dec. 9, 2014, which are incorporated herein by reference in their entireties.

FIELD OF THE INVENTION

The present invention relates to communication technologies, and particularly to a method and apparatus for processing a wearing state of a wearable device.

BACKGROUND OF THE INVENTION

A wearable device is a portable device which is directly worn on a body and integrated on a user's clothes or accessory, for example, a smart bracelet, a smart watch, a smart necklace, smart glasses, a smart finger ring or the like. The wearable device is not only a hardware device, but also performs a powerful function by virtue of technologies such as software supporting and data interaction. The wearable device will bring about great changes to people's life and perception.

However, due to the user's randomness in wearing the wearable device, an actual wearing state of the wearable device is inconsistent with an ideal wearing state, and therefore cannot meet an operation demand of the wearable device, for example, a demand for collecting data of a designated position of a human body, thereby causing reduction of reliability of the wearable device. Hence, it is desirable to propose a method for acquiring a wearing state of the wearable device to determine whether the actual wearing state of the wearable device is consistent with the ideal wearing state.

SUMMARY OF THE INVENTION

A plurality of aspects of the present invention provides a method and apparatus for processing a wearing state of a wearable device to obtain a wearing state of a wearable device.

According to one aspect of the present invention, there is provided a method for processing a wearing state of a wearable device, comprising:

obtaining a space quaternion parameter of the wearable device worn by a user;

obtaining a posture angle of the wearable device according to the space quaternion parameter;

obtaining a measurement wearing state of the wearable device according to the posture angle of the wearable device.

The above-mentioned aspect and any possible implementation mode further provide an implementation mode. The obtaining a space quaternion parameter of the wearable device worn by a user comprises:

using a first sensor device to obtain the space quaternion parameter of the wearable device worn by the user; or using a second sensor device to obtain sensing data of the wearable device worn by the user; and obtain the space quaternion parameter according to the sensing data.

The above-mentioned aspect and any possible implementation mode further provide an implementation mode. The posture angle of the wearable device includes a roll angle of the wearable device; the obtaining a measurement wearing state of the wearable device according to the posture angle of the wearable device comprises:

obtaining a wearing angle of the wearable device according to the roll angle of the wearable device when a wearing body position is located at a first position.

The above-mentioned aspect and any possible implementation mode further provide an implementation mode. The obtaining a measurement wearing state of the wearable device according to the posture angle of the wearable device further comprises:

obtaining a rotation change amount of the wearable device according to the roll angle of the wearable device when the wearing body position is located at the first position and the roll angle of the wearable device when the wearing body position is located at the second position;

obtaining a rotation direction of the wearable device according to the rotation change amount of the wearable device; and obtaining the wearing position of the wearable device according to the rotation direction of the wearable device.

The above-mentioned aspect and any possible implementation mode further provide an implementation mode. The wearing position includes a left arm or a right arm; after obtaining a rotation change amount of the wearable device according to the roll angle of the wearable device when the wearing body position is located at the first position and the roll angle of the wearable device when the wearing body position is located at the second position, the method further comprises:

obtaining a position of the wearable device at the wearing position according to a distance between an elbow portion and a wrist portion, a rotation angle of the elbow portion when the wrist portion rotates by 180°, and the rotation change amount of the wearable device.

The above-mentioned aspect and any possible implementation mode further provide an implementation mode. After obtaining a measurement wearing state of the wearable device according to the posture angle of the wearable device further, the method further comprises:

obtaining a standard wearing state of the wearable device;

generating a wearing adjustment indication according to the standard wearing state and the measurement wearing state to indicate the user to adjust the wearable device; and outputting the wearing adjustment instruction; or generating a data adjustment indication according to the standard wearing state and the measurement wearing state to enable adjustment of measurement data collected by the wearable device according to the data adjustment indication.

According to another aspect of the present invention, there is provided an apparatus for processing a wearing state of a wearable device, comprising:

a collecting unit configured to obtain a space quaternion parameter of a wearable device worn by a user;

a converting unit configured to obtain a posture angle of the wearable device according to the space quaternion parameter;

a processing unit configured to obtain a measurement wearing state of the wearable device according to the posture angle of the wearable device.

The above-mentioned aspect and any possible implementation mode further provide an implementation mode. The collecting unit is specifically used to:

use a first sensor device to obtain the space quaternion parameter of the wearable device worn by the user, or use a second sensor device to obtain sensing data of the wearable device worn by the user; and obtain the space quaternion parameter according to the sensing data.

The above-mentioned aspect and any possible implementation mode further provide an implementation mode. The posture angle of the wearable device includes a roll angle of the wearable device; the processing unit is specifically used to:

obtain a wearing angle of the wearable device according to the roll angle of the wearable device when a wearing body position is located at a first position.

The above-mentioned aspect and any possible implementation mode further provide an implementation mode. The processing unit is used to obtain a rotation change amount of the wearable device according to the roll angle of the wearable device when the wearing body position is located at the first position and the roll angle of the wearable device when the wearing body position is located at the second position;

obtain a rotation direction of the wearable device according to the rotation change amount of the wearable device; and obtain the wearing position of the wearable device according to the rotation direction of the wearable device.

The above-mentioned aspect and any possible implementation mode further provide an implementation mode. The wearing position includes a left arm or a right arm; the processing unit is further used to obtain a position of the wearable device at the wearing position according to a distance between an elbow portion and a wrist portion, a rotation angle of the elbow portion when the wrist portion rotates by 180°, and the rotation change amount of the wearable device.

The above-mentioned aspect and any possible implementation mode further provide an implementation mode. The processing unit is further used to obtain a standard wearing state of the wearable device;

generate a wearing adjustment indication according to the standard wearing state and the measurement wearing state to indicate the user to adjust the wearable device; and output the wearing adjustment instruction; or generate a data adjustment indication according to the standard wearing state and the measurement wearing state to enable adjustment of measurement data collected by the wearable device according to the data adjustment indication.

As known from the above technical solutions, embodiments of the present invention achieve the purpose of obtaining an actual wearing state of the wearable device by obtaining the space quaternion parameter of the wearable device worn by the user, then obtaining the posture angle of the wearable device according to the space quaternion parameter, and then obtaining the measurement wearing state of the wearable device according to the posture angle of the wearable device.

In addition, the technical solution according to the present invention is employed to, after obtaining the measurement wearing state of the wearable device, obtain a standard wearing state of the wearable device, then generate and output a wearing adjustment indication according to the standard wearing state and the measurement wearing state to indicate the user to adjust the wearable device. As such, the user may adjust the worn wearable device according to the wearing adjustment indication, can avoid the problem in the prior art that inconsistency of the actual wearing state and the ideal wearing state of the wearable device causes failure to meet the working needs of the wearable device, and can effectively improve reliability of the wearable device.

In addition, the technical solution according to the present invention is employed to, after obtaining the measurement wearing state of the wearable device, obtain a standard wearing state of the wearable device, then generate a data adjustment indication according to the standard wearing state and the measurement wearing state to enable adjustment of measurement data collected by the wearable device according to the data adjustment indication. As such, it is possible to adjust measurement data collected by the wearable device according to the data adjustment indication, avoid the problem in the prior art that inconsistency of the actual wearing state and the ideal wearing state of the wearable device causes failure to meet the working needs of the wearable device, and effectively improve reliability of the wearable device.

BRIEF DESCRIPTION OF DRAWINGS

To describe technical solutions of embodiments of the present invention more clearly, figures used in depictions of the embodiments or the prior art will be described briefly. Obviously, the figures described below are only some embodiments of the present invention. Those having ordinary skill in the art appreciate that other figures may be obtained from these figures without making any inventive efforts.

DETAILED DESCRIPTION OF PREFERRED EMBODIMENTS

Technical solutions in embodiments of the present invention will be described clearly and completely in conjunction with figures in embodiments of the present invention to make objects, technical solutions and advantages of embodiments of the present invention clearer. Obviously, the described embodiments are partial embodiments of the present invention, not all embodiments. Based on embodiments in the present invention, all other embodiments obtained by those having ordinary skill in the art without making inventive efforts all fall within the protection scope of the present invention.

It is appreciated that the terminal involved in embodiments of the present invention may include but not limited to a mobile phone, a Personal Digital Assistant (PDA), a wireless handheld device, a tablet computer, a personal computer (PC), an MP3 player, an MP4 player, a wearable device (e.g., smart glasses, a smart watch, a smart bracelet) and the like.

In addition, the term "and/or" used in the text is only an association relationship depicting associated objects and represents that three relations might exist, for example, A and/or B may represents three cases, namely, A exists individually, both A and B coexist, and B exists individually. In addition, the symbol "/" in the text generally indicates associated objects before and after the symbol are in an "or" relationship.

Figure 1:
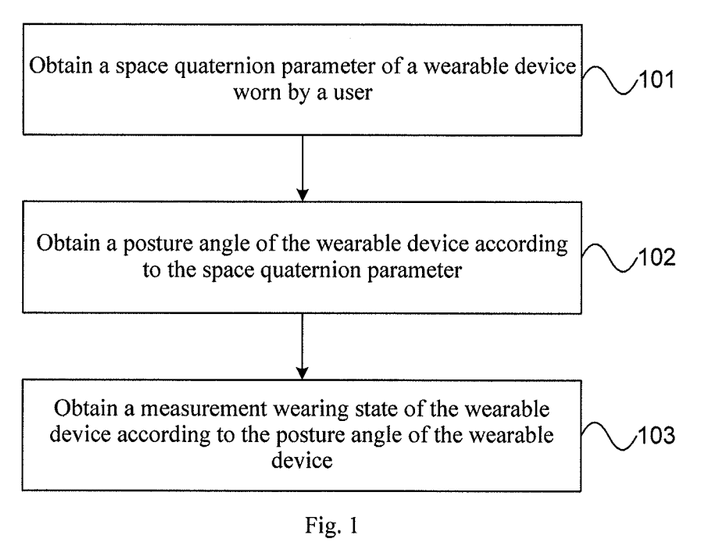
FIG. 1 is a flow chart of a method of processing a wearing state of a wearable device according to an embodiment of the present invention.

FIG. 1 is a flow chart of a method of processing a wearing state of a wearable device according to an embodiment of the present invention, as shown in FIG. 1.

101: obtaining a space quaternion parameter of a wearable device worn by a user.

102: obtaining a posture angle of the wearable device according to the space quaternion parameter.

103: obtaining a measurement wearing state of the wearable device according to the posture angle of the wearable device.

It is appreciated that partial or all executors of steps 101-103 may be applications located at a native terminal, or function units such as plug-ins or Software Development Kit (SDK) arranged in applications located at the native terminal, or processing engines located in a network-side server, or distributed systems located on the network side. The present embodiment does not particularly limit in this regard.

It may be appreciated that the application may be a native application (nativeApp) installed on the terminal, or a webpage application (webApp) of a browser on the terminal. This is not limited in the present embodiment.

As such, the purpose of obtaining an actual wearing state of the wearable device is achieved by obtaining the space quaternion parameter of the wearable device worn by the user, then obtaining the posture angle of the wearable device according to the space quaternion parameter, and then obtaining the measurement wearing state of the wearable device according to the posture angle of the wearable device.

Optionally, in a possible implementation mode of the present embodiment, in step 101, a sensor device may be specifically used to obtain the space quaternion parameter of the wearable device worn by a user. The sensor device is fixedly disposed on the wearable device and at a fixed and invariable position relative to the wearable device.

In a specific implementation procedure, the sensor device may be a first sensor device of an inertia measurement unit having a space quaternion synthesis function. In step 101, the first sensor device may be specifically used to obtain the space quaternion parameter of the wearable device worn by the user.

Wherein, the first sensor device is an inertia measurement unit having a space quaternion synthesis function, and may include but not limited to at least one kind of sensor of a three-axis acceleration sensor, a three-axis gyro and a three-axis magnetic sensor. The inertia measurement unit may specifically perform fusion processing according to collected sensing data to obtain the space quaternion parameter of the wearable device. Correspondingly, if the inertia measurement unit only includes one kind of sensor, the sensing data of the wearable device may be three-axis sensing data; if the inertia measurement unit includes two kinds of sensors, the sensing data of the wearable device may be six-axis sensing data; if the inertia measurement unit includes three kinds of sensors, the sensing data of the wearable device may be nine-axis sensing data. This is not particularly limited in the present embodiment.

In another specific implementation procedure, the sensor device may be a second sensor device of an inertia measurement unit without a space quaternion synthesis function. In step 101, the second sensor device may be specifically used to obtain the sensing data of the wearable device worn by the user; and the space quaternion parameter is obtained according to the sensing data. Specifically, it is feasible to perform fusion processing according to collected sensing data to obtain the space quaternion parameter of the wearable device. Reference may be made to relevant content in the prior art for detailed depictions, which will not be detailed here.

Wherein the second sensor device is an inertia measurement unit without a space quaternion synthesis function, and may include but not limited to at least one kind of sensor of a three-axis acceleration sensor, a three-axis gyro and a three-axis magnetic sensor. Correspondingly, if the inertia measurement unit only includes one kind of sensor, the sensing data of the wearable device may be three-axis sensing data; if the inertia measurement unit includes two kinds of sensors, the sensing data of the wearable device may be six-axis sensing data; if the inertia measurement unit includes three kinds of sensors, the sensing data of the wearable device may be nine-axis sensing data. This is not particularly limited in the present embodiment.

Optionally, in a possible implementation mode of the present embodiment, in step 102, the obtained posture angle of the wearable device may comprise at least one of heading angle, pitch angle and roll angle.

The so-called posture angle of the wearable device may be used to indicate a placement state of the wearable device at the user's certain position. Generally, a certain reference position on the wearable device, e.g., a position where the sensor device lies, may be defined as a reference position, and rightward, forward and upward directions of the reference position constitute a right-hand system. Rotation about a forward axis is the roll, rotation about a rightward axis is the pitch, and rotation about an upward axis is the heading. The rightward axis may be marked as x axis of the wearable device, the forward axis marked as y axis of the wearable device, and the upward axis marked as z axis of the wearable device. Then, the heading angle may refer to an angle between y axis of the wearable device and due north and is in a range of 0-360°; the pitch angle may refer to an angle between y axis of the wearable device and a horizontal plane and is in a range of −90°-90°; the roll angle may refer to an angle between x axis of the wearable device and a horizontal plane and is in a range of −180°-180°.

Figures 2, 3:
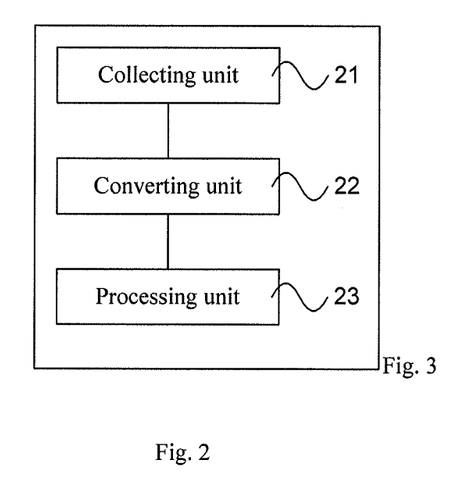
FIG. 2 is a structural schematic view of an apparatus for processing a wearing state of a wearable device according to another embodiment of the present invention.
FIG. 3 is a schematic view showing wearing of a smart bracelet in the embodiment corresponding to FIG. 1.
Figure 3:
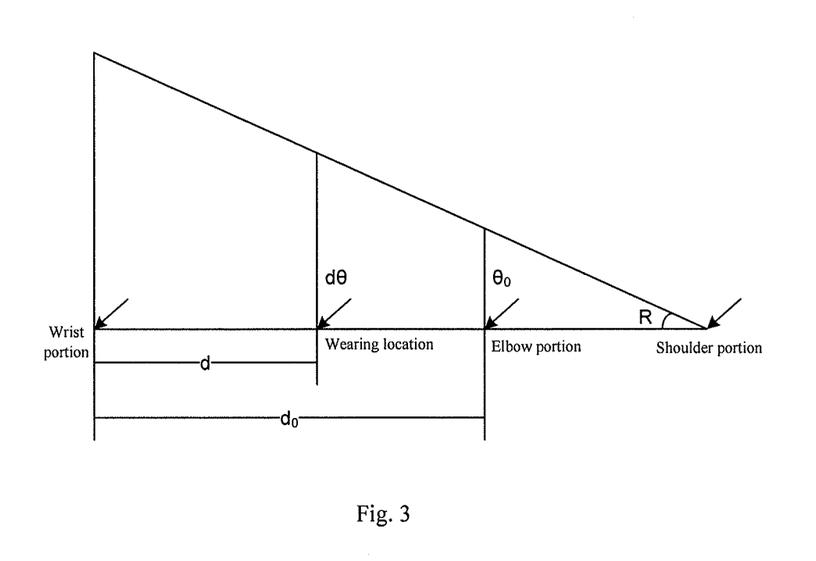

Take a smart bracelet as an example. As shown in FIG. 3, a position of the sensor device on the smart bracelet may be defined as a reference position, and rightward, forward and upward directions of the reference position constitute a right-hand system. Rotation about a forward axis is the roll, rotation about a rightward axis is the pitch, and rotation about an upward axis is the heading. The rightward axis may be marked as x axis of the smart bracelet, the forward axis marked as y axis of the smart bracelet, and the upward axis marked as z axis of the smart bracelet. Then, the heading angle may refer to an angle between y axis of the smart bracelet and due north and is in a range of 0-360°; the pitch angle may refer to an angle between y axis of the smart bracelet and a horizontal plane and is in a range of −90°-90°; the roll angle may refer to an angle between x axis of the smart bracelet and a horizontal plane and is in a range of −180°-180°. The reference position may be 0-180° on one side of the smart bracelet as divided in a vertical direction, and may be −180°-0° on the other side.

In a specific implementation procedure, the obtained space quaternion parameter of the wearable device may be specifically represented as $Q(q_0, q_1, q_2, q_3)=q_0+q_1i+q_2j+q_3k$, and furthermore, a coordinate transformation matrix $C_b^R$ resulting from rotation from a body coordinate system b (namely, a coordinate system of the wearable device) to a geographic coordinate system R is obtained according to the space quaternion parameter, namely, $$C_b^R = \begin{bmatrix} q_0^2+q_1^2-q_2^2-q_3^2 & 2(q_1q_2-q_0q_3) & 2(q_1q_3+q_0q_2) \\ 2(q_1q_2+q_0q_3) & q_0^2-q_1^2+q_2^2-q_3^2 & 2(q_2q_3-q_0q_1) \\ 2(q_1q_3-q_0q_2) & 2(q_2q_3+q_0q_1) & q_0^2-q_1^2-q_2^2+q_3^2 \end{bmatrix}.$$

It may be represented as $$C_b^R = \begin{bmatrix} T_{11} & T_{12} & T_{13} \\ T_{21} & T_{22} & T_{23} \\ T_{31} & T_{32} & T_{33} \end{bmatrix}.$$

Since during rotation from R system to b system, the coordinate system always remains a right-angle coordinate system, $C_b^R$ is an orthogonal matrix and represented as $$C_R^b = (C_b^R)^T = \begin{bmatrix} T_{11} & T_{21} & T_{31} \\ T_{12} & T_{22} & T_{32} \\ T_{13} & T_{23} & T_{33} \end{bmatrix}.$$

Then, the posture angle of the wearable device is obtained according to relationship between the coordinate transformation matrix $C_b^R$ and a strapdown posture matrix:

The roll angle of the wearable device is θ, namely, $$\theta = \tan^{-1}\left(-\frac{T_{31}}{T_{33}}\right)$$

The heading angle of the wearable device is ψ, namely, $$\psi = \tan^{-1}\frac{T_{12}}{T_{22}}$$

The pitch angle of the wearable device is φ, namely, $$\varphi = \sin^{-1} T_{32}$$

Optionally, in a possible implementation mode of the present embodiment, the posture angle of the wearable device may be the roll angle of the wearable device.

Correspondingly, in step 103, a wearing angle of the wearable device may be specifically obtained according to the roll angle when a wearing position of the wearable device worn on the body is at a first position.

In a specific implementation procedure, after the user duly wears the wearable device, the body position for wearing the wearable device is located at the first position, and kept at this position for a period of time. Within this period of time, a series of space quaternion parameters of the wearable device worn by the user is obtained according to a sampling frequency, and thereby the roll angle when the wearable device is at the first position is obtained respectively according to these space quaternion parameters. As such, a statistic value may be obtained according to all obtained roll angles of the wearable device at the first position, for example, a middle position or an average value, and then the statistic value is regarded as the wearing angle of the wearable device.

Take the smart bracelet as an example. After the user wears the smart bracelet duly, he extends straight the arm on which the smart bracelet is worn, with the palm being parallel to the ground and a center of the palm facing towards the ground, and remains at this position, called position A, for a period of time such as five seconds. Within this period of time, a series of roll angles of the smart bracelet at position A is obtained according to the sampling frequency. As such, a statistic value, for example, a middle position or an average value, may be obtained according to all obtained roll angles of the smart bracelet at the position A, and then the statistic value is regarded as the wearing angle of the smart bracelet.

In another specific implementation procedure, a jitter threshold amax of the three-axis acceleration sensor may be further pre-set. The jitter threshold amax may specifically be an empirical value such as 0.2 g (g is an acceleration of gravity) to ensure stability of the collected sensing data. After the user duly wears the wearable device, the body position for wearing the wearable device is located at the first position, and kept at this position for a period of time. Within this period of time, a series of space quaternion parameters of the wearable device worn by the user is obtained according to a sampling frequency, and thereby the roll angle when the wearable device is at the first position is obtained respectively according to these space quaternion parameters. After the roll angle of the wearable device is obtained each time, judgment is made for the collected sensing data of the three-axis acceleration sensor by using the jitter threshold amax. If the collected sensing data of the three-axis acceleration sensor is smaller than the jitter threshold amax, a value of a counter will increase by one; if the collected sensing data of the three-axis acceleration sensor is greater than or equal to the jitter threshold amax, the value of the counter will be zeroed out, and meanwhile, all obtained roll angles of the wearable device at the first position will be deleted. Until the value of the counter reaches a designated threshold size may be the statistic value, namely, a middle position or an average value, obtained according to all obtained roll angles of the wearable device at the first position, and then the statistic value is regarded as the wearing angle of the wearable device.

Correspondingly, in step 103, it is feasible to further obtain a rotation change amount of the wearable device according to the roll angle of the wearable device when the wearing body position is located at the first position and the roll angle of the wearable device when the wearing body position is located at the second position, and furthermore, obtain a rotation direction of the wearable device according to the rotation change amount of the wearable device, and finally obtain the wearing position of the wearable device according to the rotation direction of the wearable device.

In a specific implementation procedure, it is also feasible to further output indication information such as indication information in the form of a vibration indication, a sound indication or a lamp light indication or the like, to indicate the user to position the body position for wearing the wearable device at the second position, and remain at the position for a period of time. Within this period of time, a series of space quaternion parameters of the wearable device worn by the user is obtained according to a sampling frequency, and thereby the roll angle when the wearable device is at the second position is obtained respectively according to these space quaternion parameters. As such, a statistic value, for example, a middle position or an average value, may be obtained according to all obtained roll angles of the wearable device at the second position, and then the statistic value is regarded as the rotation angle after the wearable device rotates. Then, a differential value between the rotation angle after the wearable device rotates and the wearing angle of the wearable device is regarded as the rotation change amount of the wearable device.

Take the smart bracelet as an example. After the user sees the indication information, he extends straight the arm on which the smart bracelet is worn, with the palm being parallel to the ground and a center of the palm facing towards the ground, then rotates the arm outward to an extent that the center of the palm faces towards the sky, and remains at this position, called position B, for a period of time such as five seconds. Within this period of time, a series of roll angles of the smart bracelet at position B is obtained according to the sampling frequency. As such, a statistic value, for example, a middle position or an average value, may be obtained according to all obtained roll angles of the smart bracelet at the position B, and then the statistic value is regarded as the rotation angle after the smart bracelet rotates. Then, a differential value between the rotation angle after the smart bracelet rotates and the wearing angle of the smart bracelet is regarded as the rotation change amount of the smart bracelet.

After the rotation change amount of the smart bracelet is obtained, a processing manner may be performing judgment for the rotation change amount of the smart bracelet. If the rotation change amount of the smart bracelet is smaller than 0, a rotation direction of the smart bracelet is obtained as a counterclockwise direction, and then the wearing position of the wearable device may be obtained as a left arm; if the rotation change amount of the smart bracelet is greater than 0, a rotation direction of the smart bracelet is obtained as a clockwise direction, and then the wearing position of the wearable device may be obtained as a right arm.

After the rotation change amount of the smart bracelet is obtained, another processing manner may be further presetting a change threshold bmax. The change threshold bmax may specifically be an empirical value 40° and is used to prevent mistriggering of judgment of the rotation direction of the smart bracelet caused by data jitter caused by tiny acts of the arm. Specifically, the preset change threshold may be used to judge the rotation change amount of the smart bracelet. If the rotation change amount of the smart bracelet is smaller than 0, and less than or equal to −bmax, the rotation direction of the smart bracelet is obtained as a counterclockwise direction, and then the wearing position of the wearable device may be obtained as a left arm; if the rotation change amount of the smart bracelet is greater than 0 and greater than or equal to bmax, a rotation direction of the smart bracelet is obtained as a clockwise direction, and then the wearing position of the wearable device may be obtained as a right arm. Otherwise, the rotation change amount of the smart bracelet is greater than −bmax and smaller than bmax, the rotation change amount of the smart bracelet is re-calculated.

In another specific implementation procedure, the wearing position of the wearable device may include a left arm or a right arm; correspondingly, in step 103, it is feasible to further obtain the position of the wearable device at the wearing position according to a distance between an elbow portion and a wrist portion, a rotation angle of the elbow portion when the wrist portion rotates by 180°, and the rotation change amount of the wearable device.

Wherein, the distance between the elbow portion and the wrist portion and the rotation angle of the elbow portion when the wrist portion rotates by 180° may be a preset empirical value and may be set flexibly respectively for different user subjects such as children, youngsters, males, females and the like.

Figure 4:
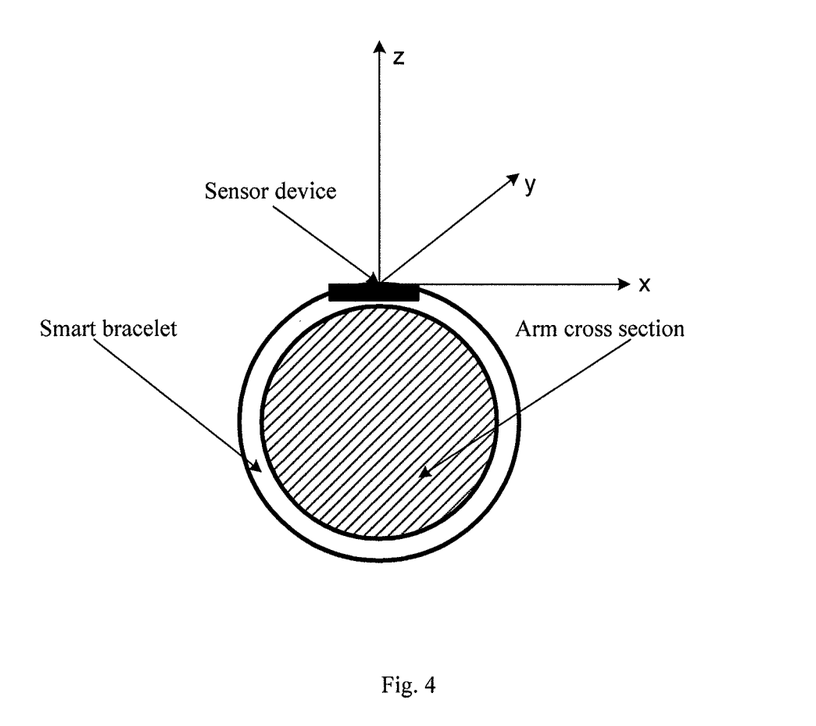
FIG. 4 is a schematic view showing calculation of a wearing position of the wearable device in the embodiment corresponding to FIG. 1.

For example, when the arm makes a longitudinal rotation action, i.e., when the user extends straight the arm on which the wearable device is worn, with the palm being parallel to the ground and a center of the palm facing towards the ground, then rotates the arm outward to an extent that the center of the palm faces towards the sky, two parameters, namely, axial rotation angle and longitudinal position of each point along the longitudinal axis of the arm, may satisfy a certain relationship, e.g., a linear relationship, or again for example, a nonlinear relationship such as a trigonometric function. Usually, the rotation angle of the write portion is maximal and the rotation angle of a position adjacent to the shoulder portion is approximately 0. To simplify processing, the linear relationship between the axial rotation angle and longitudinal position of each point along the longitudinal axis of the arm is approximately processed as a trigonometric function relationship. As shown in FIG. 4, the position of the wearable device on the wearing position may be specifically obtained according to the following formula:

$$d = d_0 - \frac{d\theta - \theta_0}{\tan R};$$

wherein, d is a distance between a position of the wearable device at the wearing position and the wrist portion;

$d_0$ is a distance between the elbow portion and the wrist portion;

$d\theta$ is the rotation change amount of the wearable device;

$\theta_0$ is a rotation angle of the elbow portion when the wrist portion rotates by 180°;

R is an angle coefficient of a trigonometric function relationship, may be a preset empirical value and may be set flexibly respectively for different user subjects such as children, youngsters, males, females and the like;

tan R may take a value resulting from 180°/a distance between a shoulder portion and the wrist portion.

Wherein the distance between the shoulder portion and the wrist portion and the rotation angle of the elbow portion when the wrist portion rotates by 180° may be a preset empirical value and may be set flexibly respectively for different user subjects such as children, youngsters, males, females and the like.

So far, the measuring wearing state of the wearable device is obtained by performing the above operations, and may be specifically represented as a vector having three dimensions, namely, <wearing angle, wearing position, wearing location>.

Optionally, in a possible implementation mode of the present embodiment, after step 103, it is feasible to further obtain a standard wearing state of the wearable device, and then execute an operation of optimizing the wearable device according to the standard wearing state and the measurement wearing state.

In a specific implementation procedure, specifically it is feasible to generate a wearing adjustment indication according to the standard wearing state and the measurement wearing state to indicate the user to adjust the wearable device; and output the wearing adjustment instruction such as indication information like indication information in the form of a vibration indication, a sound indication or a lamp light indication.

As such, the user may adjust the worn wearable device according to the wearing adjustment indication, e.g., adjust a wearing angle, wearing position, wearing location and the like of the worn wearable device, can avoid the problem in the prior art that inconsistency of the actual wearing state and the ideal wearing state of the wearable device causes failure to meet the working needs of the wearable device, and can effectively improve reliability of the wearable device.

In another specific implementation procedure, specifically it is feasible to generate a data adjustment indication according to the standard wearing state and the measurement wearing state to enable adjustment of measurement data collected by the wearable device according to the data adjustment indication.

In this way, it is possible to adjust measurement data collected by the wearable device according to the data adjustment indication, avoid the problem in the prior art that inconsistency of the actual wearing state and the ideal wearing state of the wearable device causes failure to meet the working needs of the wearable device, and effectively improve reliability of the wearable device.

In the present embodiment, the purpose of obtaining an actual wearing state of the wearable device is achieved by obtaining the space quaternion parameter of the wearable device worn by the user, then obtaining the posture angle of the wearable device according to the space quaternion parameter, and then obtaining the measurement wearing state of the wearable device according to the posture angle of the wearable device.

It needs to be appreciated that for purpose of easy depictions, the above-mentioned method embodiments all are represented as a series of combinations of actions, but those skilled in the art should know that the present invention is not limited to the order of depicted actions because according to the present invention, some steps may be performed in other order or simultaneously. Secondly, those skilled in the art should also appreciate that embodiments described in the description all belong to preferred embodiments, and the involved actions and modules are not certainly requisite for the present invention.

In the above embodiments, the embodiments are depicted with different focus, and portions not depicted in a certain embodiment may be found in related depictions in other embodiments.

FIG. 2 is a structural schematic view of an apparatus for processing a wearing state of a wearable device according to another embodiment of the present invention. As shown in FIG. 2, the apparatus for processing a wearing state of a wearable device according to the present embodiment may comprise a collecting unit 21, a converting unit 22 and a processing unit 23, wherein the collecting unit 21 is configured to obtain a space quaternion parameter of a wearable device worn by a user; the converting unit 22 is configured to obtain a posture angle of the wearable device according to the space quaternion parameter; and the processing unit 23 is configured to obtain a measurement wearing state of the wearable device according to the posture angle of the wearable device.

It is appreciated that partial or all apparatuses for processing the wearing state of the wearable device according to the present embodiment may be applications located at a native terminal, or function units such as plug-ins or Software Development Kit (SDK) arranged in applications located at the native terminal, or processing engines located in a network-side server, or distributed systems located on the network side. The present embodiment does not particularly limit in this regard.

It may be appreciated that the application may be a native application (nativeApp) installed on the terminal, or a webpage application (webApp) of a browser on the terminal. This is not limited in the present embodiment.

Optionally, in a possible implementation mode of the present embodiment, the collecting unit 21 specifically may use a first sensor device to obtain the space quaternion parameter of the wearable device worn by the user.

Optionally, in a possible implementation mode of the present embodiment, the collecting unit 21 specifically may use a second sensor device to obtain sensing data of the wearable device worn by the user; and obtain the space quaternion parameter according to the sensing data.

Optionally, in a possible implementation mode of the present embodiment, the posture angle of the wearable device may include a roll angle of the wearable device; correspondingly, the processing unit 23 may specifically be used to obtain a wearing angle of the wearable device according to the roll angle of the wearable device when a wearing body position is located at a first position.

In a specific implementation procedure, the processing unit 23 may be further used to obtain a rotation change amount of the wearable device according to the roll angle of the wearable device when the wearing body position is located at the first position and the roll angle of the wearable device when the wearing body position is located at the second position; obtain a rotation direction of the wearable device according to the rotation change amount of the wearable device; and obtain the wearing position of the wearable device according to the rotation direction of the wearable device.

Specifically, the wearing position includes a left arm or a right arm; correspondingly, the processing unit 23 may be further used to obtain a position of the wearable device at the wearing position according to a distance between an elbow portion and a wrist portion, a rotation angle of the elbow portion when the wrist portion rotates by 180°, and the rotation change amount of the wearable device.

Optionally, in a possible implementation mode of the present embodiment, the processing unit 23 may be further used to obtain a standard wearing state of the wearable device; generate a wearing adjustment indication according to the standard wearing state and the measurement wearing state to indicate the user to adjust the wearable device; and output the wearing adjustment instruction; or generate a data adjustment indication according to the standard wearing state and the measurement wearing state to enable adjustment of measurement data collected by the wearable device according to the data adjustment indication.

Noticeably, the method in the method corresponding to FIG. 1 may be implemented by the apparatus for processing the wearing state of the wearable device according to the present embodiment. Reference may be made to relevant content in the embodiment corresponding to FIG. 1 for detailed depictions, which will not be detailed here.

In the present embodiment, the purpose of obtaining an actual wearing state of the wearable device is achieved by obtaining the space quaternion parameter of the wearable device worn by the user, then obtaining the posture angle of the wearable device according to the space quaternion parameter, and then obtaining the measurement wearing state of the wearable device according to the posture angle of the wearable device.

In addition, the technical solution according to the present invention is employed to, after obtaining the measurement wearing state of the wearable device, obtain a standard wearing state of the wearable device, then generate and output a wearing adjustment indication according to the standard wearing state and the measurement wearing state to indicate the user to adjust the wearable device. As such, the user may adjust the worn wearable device according to the wearing adjustment indication, can avoid the problem in the prior art that inconsistency of the actual wearing state and the ideal wearing state of the wearable device causes failure to meet the working needs of the wearable device, and can effectively improve reliability of the wearable device.

In addition, the technical solution according to the present invention is employed to, after obtaining the measurement wearing state of the wearable device, obtain a standard wearing state of the wearable device, then generate a data adjustment indication according to the standard wearing state and the measurement wearing state to enable adjustment of measurement data collected by the wearable device according to the data adjustment indication. As such, it is possible to adjust measurement data collected by the wearable device according to the data adjustment indication, avoid the problem in the prior art that inconsistency of the actual wearing state and the ideal wearing state of the wearable device causes failure to meet the working needs of the wearable device, and effectively improve reliability of the wearable device.

Those skilled in the art can clearly understand that for the sake of convenience and brevity of depictions, reference may be made to corresponding procedures in the above-mentioned method embodiments for specific working procedures of the system, apparatus and unit described above.

In the embodiments of the present invention, it should be understood that the system, apparatus and method disclosed can be implemented in other ways. For example, the above-mentioned apparatus embodiments are only illustrative, e.g., the division of the units is merely logical one, and, in reality, they can be divided in other ways. For example, a plurality of units or components may be combined or integrated into another system, or some features may be neglected or not executed. In addition, mutual coupling or direct coupling or communication connection as displayed or discussed may be performed via some interfaces, and indirect coupling or communication connection of means or units may be electrical, mechanical or in other forms.

The units described as separate parts may be or may not be physically separated, the parts shown as units may be or may not be physical units, i.e., they can be located in one place, or distributed in a plurality of network units. One can select some or all the units to achieve the purpose of the embodiment according to the actual needs.

Further, in the embodiments of the present invention, functional units can be integrated in one processing unit, or they can be separate physical presences; or two or more units can be integrated in one unit. The integrated unit described above can be realized as hardware, or they can be realized with hardware and software functional unit.

The aforementioned integrated unit in the form of software function units may be stored in a computer readable storage medium. The aforementioned software function units are stored in a storage medium, including several instructions to instruct a computer device (a personal computer, server, or network equipment, etc.) or processor to perform some steps of the method described in the various embodiments of the present invention. The aforementioned storage medium includes various media that may store program codes, such as U disk, removable hard disk, read-only memory (ROM), a random access memory (RAM), magnetic disk, or an optical disk.

Finally, it is appreciated that the above embodiments are used to illustrate technical solutions of the present invention, not intended to limit the present invention. Although the present invention is described in detail with reference to the aforesaid embodiments, those having ordinary skill in the art should appreciate that they still may modify technical solutions disclosed in the embodiments, or equivalently substitute partial technical features therein; these modifications or substitutions do not make the essence of corresponding technical solutions depart from the spirit and scope of technical solutions of the embodiments of the present invention.

What is claimed is:

1. A method for processing a wearing state of a wearable device, wherein the method comprises:
   obtaining, by an inertia measurement sensor integrated with space quaternion synthesis function, a space quaternion parameter of the wearable device worn by a user;
   obtaining, by a processing apparatus, a posture angle of the wearable device according to the space quaternion parameter;
   obtaining, by the processing apparatus, a measurement wearing state of the wearable device according to the posture angle of the wearable device;
   wherein the posture angle of the wearable device includes a roll angle of the wearable device; the obtaining of the measurement wearing state of the wearable device according to the posture angle of the wearable device comprises:
      obtaining a wearing angle of the wearable device according to the roll angle of the wearable device when a wearing body position is located at a first position;
      obtaining a rotation change amount of the wearable device according to the roll angle of the wearable device when the wearing body position is located at the first position and the roll angle of the wearable device when the wearing body position is located at the second position;
      obtaining a rotation direction of the wearable device according to the rotation change amount of the wearable device;
      obtaining a wearing position of the wearable device according to the rotation direction of the wearable device; and
   wherein the wearing position includes a left arm or a right arm; after obtaining a rotation change amount of the wearable device according to the roll angle of the wearable device when the wearing body position is located at the first position and the roll angle of the wearable device when the wearing body position is located at the second position, the method further comprises:
      obtaining a position of the wearable device at the wearing position according to a distance between an elbow portion and a wrist portion, a rotation angle of the elbow portion when the wrist portion rotates by 180°, and the rotation change amount of the wearable device.

2. The method according to claim 1, wherein after obtaining a measurement wearing state of the wearable device according to the posture angle of the wearable device, the method further comprises:

obtaining a standard wearing state of the wearable device;
generating a wearing adjustment indication according to the standard wearing state and the measurement wearing state to indicate the user to adjust the wearable device; and outputting the wearing adjustment instruction; or
generating a data adjustment indication according to the standard wearing state and the measurement wearing state to enable adjustment of measurement data collected by the wearable device according to the data adjustment indication.

3. The method of claim 1, wherein the processing apparatus is located locally at the wearable device, configured to receive the space quaternion parameter from the inertia measurement sensor.

4. The method of claim 1, wherein the processing apparatus is located remotely at a network-side server, the method further comprising:
sending the space quaternion parameter to the processing apparatus; and
receiving the measurement wearing state of the wearable device calculated by the processing apparatus from the network-side server.

5. An apparatus for processing a wearing state of a wearable device, wherein the apparatus comprises:
an inertia measurement sensor integrated with space quaternion synthesis function, configured to
obtain a space quaternion parameter of a wearable device worn by a user; and
a processor configured to
obtain a posture angle of the wearable device according to the space quaternion parameter; and
obtain a measurement wearing state of the wearable device according to the posture angle of the wearable device;
wherein the posture angle of the wearable device includes a roll angle of the wearable device; the processor is specifically used to
obtain a wearing angle of the wearable device according to the roll angle of the wearable device when a wearing body position is located at a first position;
wherein the processing is further used to
obtain a rotation change amount of the wearable device according to the roll angle of the wearable device when the wearing body position is located at the first position and the roll angle of the wearable device when the wearing body position is located at the second position;
obtain a rotation direction of the wearable device according to the rotation change amount of the wearable device; and
obtain a wearing position of the wearable device according to the rotation direction of the wearable device;

wherein the wearing position includes a left arm or a right arm; the processor is further used to
obtain a position of the wearable device at the wearing position according to a distance between an elbow portion and a wrist portion, a rotation angle of the elbow portion when the wrist portion rotates by 180°, and the rotation change amount of the wearable device.

6. The apparatus according to claim 5, wherein the processor is further used to
obtain a standard wearing state of the wearable device;
generate a wearing adjustment indication according to the standard wearing state and the measurement wearing state to indicate the user to adjust the wearable device; and output the wearing adjustment instruction; or
generate a data adjustment indication according to the standard wearing state and the measurement wearing state to enable adjustment of measurement data collected by the wearable device according to the data adjustment indication.

7. A wearable device, comprises:
an inertia measurement sensor integrated with space quaternion synthesis function, configured to
obtain a space quaternion parameter of a wearable device worn by a user; and
an apparatus for processing configured to
obtain a posture angle of the wearable device according to the space quaternion parameter, the posture angle of the wearable device includes a roll angle of the wearable device;
obtain a measurement wearing state of the wearable device according to the posture angle of the wearable device based on the roll angle of the wearable device when a wearing body position is located at a first position;
obtain a rotation change amount of the wearable device according to the roll angle of the wearable device when the wearing body position is located at the first position and the roll angle of the wearable device when the wearing body position is located at the second position;
obtain a rotation direction of the wearable device according to the rotation change amount of the wearable device;
obtain a wearing position of the wearable device according to the rotation direction of the wearable device, the wearing position includes a left arm or a right arm; and
obtain a position of the wearable device at the wearing position according to a distance between an elbow portion and a wrist portion, a rotation angle of the elbow portion when the wrist portion rotates by 180°, and the rotation change amount of the wearable device.

* * * * *